(12) United States Patent
Kurwa (10) Patent No.: US 6,592,541 B1
(45) Date of Patent: Jul. 15, 2003

(54) OPHTHALMOLOGICAL SURGICAL INSTRUMENT, DEVICE AND METHOD OF USE

(76) Inventor: Badrudin Kurwa, 301 W. Huntington Dr., No.107, Arcadia, CA (US) 91007

( * ) Notice: Subject to any disclaimer, the term of this patent is extended or adjusted under 35 U.S.C. 154(b) by 0 days.

(21) Appl. No.: 09/328,912

(22) Filed: Jun. 9, 1999

Related U.S. Application Data (60) Provisional application No. 60/118,336, filed on Feb. 3, 1999, and provisional application No. 60/093,608, filed on Jul. 21, 1998.

(51) Int. Cl.[7] ............................................. A61B 17/20
(52) U.S. Cl. ........................ 604/22; 604/35; 604/521; 604/500; 606/171; 606/169
(58) Field of Search ............................ 604/35, 22, 46, 604/48, 500, 506, 521, 290, 289, 294, 540; 606/107, 162, 167, 170, 171, 172, 178

(56) References Cited

U.S. PATENT DOCUMENTS

| 4,428,748 | A | * | 1/1984 | Peyman et al. ............... 604/22 |
| 4,773,415 | A | * | 9/1988 | Tan ............................ 600/209 |
| 4,897,079 | A | * | 1/1990 | Zaleski et al. ................ 604/22 |
| 5,047,008 | A | * | 9/1991 | De Juan, Jr. et al. ......... 604/22 |
| 5,135,481 | A | * | 8/1992 | Nemeh ......................... 604/22 |
| 5,154,694 | A | * | 10/1992 | Kelman ........................ 604/22 |
| 5,154,696 | A | * | 10/1992 | Shearing ...................... 604/22 |
| 5,156,607 | A | * | 10/1992 | Kansas ....................... 606/107 |
| 5,222,960 | A | * | 6/1993 | Poley ......................... 128/898 |
| 5,257,988 | A | * | 11/1993 | L'Esperance, Jr. ........... 604/12 |
| 5,261,883 | A | * | 11/1993 | Hood et al. .................. 604/153 |
| 5,378,150 | A | * | 1/1995 | Harrel et al. ................. 433/91 |
| 5,464,389 | A | * | 11/1995 | Stahl ........................... 604/22 |
| 5,554,155 | A | * | 9/1996 | Awh et al. .................... 606/16 |
| 5,562,612 | A | * | 10/1996 | Fox ............................. 604/27 |
| 5,591,184 | A | * | 1/1997 | McDonnell et al. ......... 606/167 |
| 5,674,235 | A | * | 10/1997 | Parisi ......................... 606/169 |
| 5,810,765 | A | * | 9/1998 | Oda ............................ 604/31 |
| 5,836,897 | A | * | 11/1998 | Sakurai et al. ................ 601/2 |
| 5,836,959 | A | * | 11/1998 | Seibel et al. ................. 606/169 |
| 5,921,999 | A | * | 7/1999 | Dilleo ......................... 606/166 |
| 5,957,914 | A | * | 9/1999 | Cook et al. .................... 606/6 |
| 5,957,921 | A | * | 9/1999 | Mirhashemi et al. ......... 606/34 |
| 6,039,565 | A | * | 3/2000 | Chou et al. .................. 433/29 |
| 6,050,971 | A | * | 4/2000 | Garnier et al. ............... 604/43 |
| 6,074,358 | A | * | 6/2000 | Andrew et al. ............... 604/28 |
| 6,159,175 | A | * | 12/2000 | Strukel et al. ................ 604/22 |
| 6,165,190 | A | * | 12/2000 | Nguyen ....................... 606/166 |

* cited by examiner

Primary Examiner—Brian L. Casler
Assistant Examiner—Cris Rodriguez
(74) Attorney, Agent, or Firm—John J. Connors; Connors & Associates, Inc.

(57) ABSTRACT

An ophthalmological device for cutting into a nucleus of a cataract comprises a phaco tip including a body having at a distal end thereof a solid blade with a face edge adapted to be placed in contact with the nucleus. There is no aspiration port in this face edge. An aspiration port in the body is displaced rearward from the face edge by a distance which is greater than the length of the blade. A sleeve fits over the body and has a forward section that terminates in an opening in advance of the aspiration port. The device is used alternately with a standard phaco tip to remove cataracts. A surgical instrument comprises a handpiece including phaco tip having a face edge having aspiration port therein that is adapted to be placed in communication with a source of aspiration. A control unit regulates the application of aspiration to the aspiration port, enabling aspiration at the aspiration port to be discontinued on command.

9 Claims, 5 Drawing Sheets

OPHTHALMOLOGICAL SURGICAL INSTRUMENT, DEVICE AND METHOD OF USE

RELATED PATENT APPLICATIONS

This utility patent application is based on provisional patent application entitled "Ultrasonic Phaco Chopper & Method," filed Jul. 21, 1998, U.S. Ser. No. 60/093,608, and provisional patent application entitled "Phaco Tip With Selectable Aspiration," filed Feb. 3, 1999, U.S. Ser. No. 60/118,336. Both of these provisional applications are incorporated herein by reference and made a part of this application.

BACKGROUND OF THE INVENTION

1. Field of the Invention

This invention relates an improved ophthalmological instrument and phaco tip device used in the removal of a cataract nucleus from an eye and an improved cataract removal method.

2. Background Discussion

The current technology for cataract removal involves the use of ultrasound to dissolve, that is, emulsify, the nucleus, the hardest part of a cataract. This approach allows the cataract nucleus to be removed by washing it out through a tiny incision as small as 3 millimeters (mm) or less. Having a small incision allows safer surgery and rapid recovery. The one drawback to this technique is that exposure to ultrasonic energy needs to be kept to a minimum. Excess exposure causes damage to the very sensitive cornea. The chance of this happening is more likely when a cataract is dense or very hard. Long ultrasonic time exposures when trying to emulsify dense cataract nuclei may result in corneal damage and other complications.

It has been found that if the nucleus can first be segmented into smaller pieces, such as quarters, the ultrasonic exposure time can be greatly reduced even for very dense cataracts. The simplest approach to quartering the nucleus has been to use the regular ultrasonic emulsifier to cut a deep groove in the middle of the nucleus in an anterior posterior direction. The nucleus is then rotated 90 degrees and another groove cut deeply at right angles to the first groove, thus creating a "cross" pattern. Typically these grooves are about 1 to 1.5 millimeters in width and 3 millimeters deep, and intersect at about the center of the nucleus. Using a cracking device such as Katena nucleus splitters, the nucleus is then split into four quarters and each quarter removed by ultrasonic emulsification. A conventional phaco tip using ultrasonic energy for cutting these grooves comprises a hollow needle, having a passageway with a 1 mm to 1.5 mm diameter. Thus, the groove being cut is also equal to the tip diameter and is about 1 mm to 1.5 mm wide. The central opening in the ultrasonic tip is used to aspirate the emulsified and liquefied nucleus out of the eye as the emulsification proceeds.

Because the phaco tips used so far are 1 mm to 1.5 mm wide, the ultrasonic energy expended to cut through very hard nucleus is excessive, thus occasionally causing severe damage to the cornea. Also the nucleus may be too hard and simply not be able to be cut with such a conventional phaco tip. Thus, there may at times be a risk of dislocating the entire nucleus into the posterior region of the eye. Often under such conditions the ultrasonic procedure has to be abandoned and the surgeon has to resort to the old fashioned technique of opening the eye extensively with a knife to extract the cataract in its entirety, leading to a complicated prolonged surgical outcome.

In order to circumvent these above difficulties, Dr. Nagahara some years ago developed the concept of "natural cleavage planes" existing in the nucleus that could be used to advantage to essentially split (or chop, as he called it) the nucleus into two pieces by simply pushing a hook through the nucleus center. Although this technique has been popularized in the last few years, many surgeons still find it very difficult to use reliably.

More recently, a pre-chopper was introduced by Dr. Akoshi. The idea behind this pre-chopper was to make a very sharp pointed set of paddles in the form of a cross action forceps that could be pushed into the center of the nucleus and then pressed apart against each other, thus splitting the nucleus into 2 pieces. The difficulty has been that this pre-chopper only works well when the nucleus has a density neither too hard nor too soft. If the nucleus happens to be very soft, the paddles simply cause the nucleus material to get "mushed" without a splitting action. If the nucleus is anywhere too hard, the pre-chopper cannot be pushed into its center, deeply enough to split the nucleus. There is a serious risk of dislocation of the nucleus if further pressure is exerted. Very hard nucleus that will require excessive ultrasonic time exposure cannot be split with a pre-chopper.

All current phaco manufacturers have focused on making phaco machines more and more sophisticated with more available ultrasonic power, more vacuum, more pedals, and other features. Considering the steps involved in one of the more popular approaches to nucleus removal, the groove and crack approach, there are clearly at least two distinct steps involved that require the use of ultrasonic energy. The first step is to break the nucleus into smaller segments (usually quarters) and then to debulk, or remove each piece by emulsification. Breaking the nucleus into segments is achieved by deeply grooving the nucleus and then cracking the nucleus manually either with the standard phaco handpiece and another instrument (2 handed approach) or with a nucleus cracker (Katena, Rhein, etc.) in a one handed approach. The debulking step is performed with the same phaco tip used for making the initial grooves. It is a very inefficient in breaking the nucleus and debulking.

There are several disadvantages in using a standard single tip approach. Using one standard tip for both grooving the nucleus and debulking the segments is a very inefficient approach. In soft nuclei this approach manages to work, but when faced with a very hard nucleus, even a 45 degree beveled tip or a Kelman tip can take several minutes of phaco time to cut a groove deep enough. This also puts severe stress on the zonules. A phaco tip designed primarily for debulking, as all current tips are, works poorly as a cutting tool. To attempt to enhance the cutting action, manufacturers have advocated putting a 30 or 45 degree bevel to the tip. This improves the cutting characteristics of the tip, but exposes the cornea endothelial to excessive ultrasonic energy being released from the bevel face up position that is currently advocated. All currently available tips are 1–1.5 mm in diameter to allow for adequate aspiration of the released debris. When such a tip is used initially to just cut a groove, only the apex of the beveled tip is in contact with and is actually cutting nucleus. The greater portion of the face of the vibrating tip is in aqueous with the bevel facing upwards, thus transmitting most of the ultrasonic energy directly towards the cornea endothelium. Since the conventional phaco tip has ongoing aspiration, the tip has to be used with the bevel face up, thus directing a large part of the ultrasonic energy directly towards the corneal endothelium rather than into the cataract nucleus that needs to be cut.

SUMMARY OF THE INVENTION

This invention has several features, no single one of which is solely responsible for its desirable attributes. Without limiting the scope of this invention as expressed by the claims that follow, its more prominent features will now be discussed briefly. After considering this discussion, and particularly after reading the section entitled, "DETAILED DESCRIPTION OF THE PREFERRED EMBODIMENTS," one will understand how the features of this invention provide its benefits, which include, but are not limited to, safer surgical techniques, greater control by the surgeon during cataract removal, and reduction in damage to tissue during surgery.

This invention includes an ophthalmological device for cutting into a nucleus of a cataract. It employs a unique phaco tip. The first feature of this ophthalmological device is that the phaco tip has a body with a solid blade at its distal end. The solid blade has a face edge adapted to be placed in contact with the nucleus. This face edge is characterized in that it does not have any aspiration port therein. The face edge preferably has a surface area from about 0.4 to about 0.8 square millimeters, and a thickness from about 0.01 to about 0.6 millimeters. The width and height dimensions of the face edge at their greatest dimensions do not exceed the width and height dimensions of the body of the phaco tip.

The second feature is that the blade has a length which does not exceed 5.0 millimeters, preferably having a length of from about 2.0 to about 5.0 millimeters, a height which does not exceed 3.0 millimeters, preferably having a height of from about 1.0 to about 3.0 millimeters, and a thickness which does not exceed 0.6 millimeter, preferably having a thickness of from about 0.1 to about 0.6 millimeters.

The third feature is that the body has an aspiration port therein displaced rearward from the face edge by a distance greater than the length of the blade. This aspiration port is positioned on the body to point away from the nucleus when the face edge is placed in contact with the nucleus. A sleeve fits over the body of the phaco tip and has a forward section that terminates in an opening in advance of the aspiration port, so that the sleeve does not cover the aspiration port.

The fourth feature is that the blade may be beveled or blunt. When beveled, the bevel is at an angle from about 30° to about 45°. The blade may also have different shapes, for example, a chisel shape or a claw shape.

This invention also includes a surgical instrument for removing a nucleus of a cataract from beneath the cornea of an eye. The instrument comprises a source of aspiration, and a handpiece including phaco tip having a face edge adapted to be placed in contact with the nucleus. The face edge has aspiration port therein that is adapted to be placed in communication with the source of aspiration. A control unit regulates the application of aspiration to the aspiration port, enabling aspiration at the aspiration port to be turned on and off on command. This instrument allows the surgeon to only apply aspiration when needed. Consequently, aspiration is turned off when cracking the nucleus.

This instrument is made by modifying a conventional phaco control unit so that it includes a manually operable control element such as a switch that enables a surgeon to selectively turn on and off aspiration at the phaco tip. Preferably, a switch is incorporated in a foot pedal. Employing the "groove and crack" approach, using either the unique phaco tip of this invention or a conventional phaco tip to crack the nucleus, the surgeon selectively turns aspiration on and off, drawing cataract debris into the aspiration passageway.

This invention also includes methods of removing a nucleus of a cataract from beneath the cornea of an eye.

One method includes:
(a) making an opening in the eye to provide access to the nucleus and allow insertion through the opening of a distal end of a first phaco tip having a solid blade with a face edge adapted to be placed in contact with the nucleus, said face edge characterized in that it does not have any aspiration port therein,
(b) inserting the blade of the first phaco tip through the opening and providing ultrasonic energy to the blade while making at least one incision with the blade in the nucleus, said incision having internal walls,
(c) cracking the nucleus by inserting into the incisions an instrument which is manually manipulated to apply pressure against the internal walls of the incision to break the nucleus into segments, and
(d) inserting through the opening a second phaco tip including an aspiration port therein and applying aspiration while emulsifying the segments and withdrawing the emulsified segments through the aspiration port.

This one method may include irrigating the nucleus with water, which exits through the opening.

Another method includes:
(a) making an opening in the eye to provide access to the nucleus and allow insertion through the opening of a distal end of a phaco tip having a face edge adapted to be placed in contact with the nucleus, said face edge having and aspiration port therein, said aspiration port being in communication with a source of aspiration that can be selectably applied and discontinued under the control of a surgeon conducting the method,
(b) inserting the blade of the phaco tip through the opening and providing ultrasonic energy to the blade while making at least one incision with the blade in the nucleus and simultaneously discontinuing aspiration as the incision is being made, said incision having internal walls,
(c) cracking the nucleus by inserting into the incisions an instrument which is manually manipulated to apply pressure against the internal walls of the incision to break the nucleus into segments, and
(d) applying aspiration to the aspiration port while emulsifying the segments and withdrawing the emulsified segments through the aspiration port.

In practicing the above methods the surgeon makes a cross incision having a depth that does not to exceed about 3 millimeters, and the nucleus is mobilized so that it may be rotated substantially 90 degrees. The eye is irrigated with fluid flowing out the sleeve, over the nucleus, and exiting through the corneal opening.

DESCRIPTION OF THE DRAWING

The preferred embodiments of this invention, illustrating all its features, will now be discussed in detail. These embodiments depict the novel and non-obvious surgical instrument, ophthalmological device and method of this invention as shown in the accompanying drawing, which is for illustrative purposes only. This drawing includes the following Figures (FIGS.), with like numerals indicating like parts:

FIG. 7E' is a schematic illustration of the step 5, showing forceps inserted into a groove cut into the nucleus by the device of this invention.

DETAILED DESCRIPTION OF THE PREFERRED EMBODIMENTS

The present invention involves two parts. First, new types of phaco tips 10, 20, 30, 40, 50, and 60, respectively shown in FIGS. 1, 4A, 4B, 5A, 5B, and 6, and second, modifications to the main power unit shown in FIG. 8 that provides selective aspiration to a phaco handpiece.

First Embodiment of Phaco Tip

Figures 1, 2, 4B:
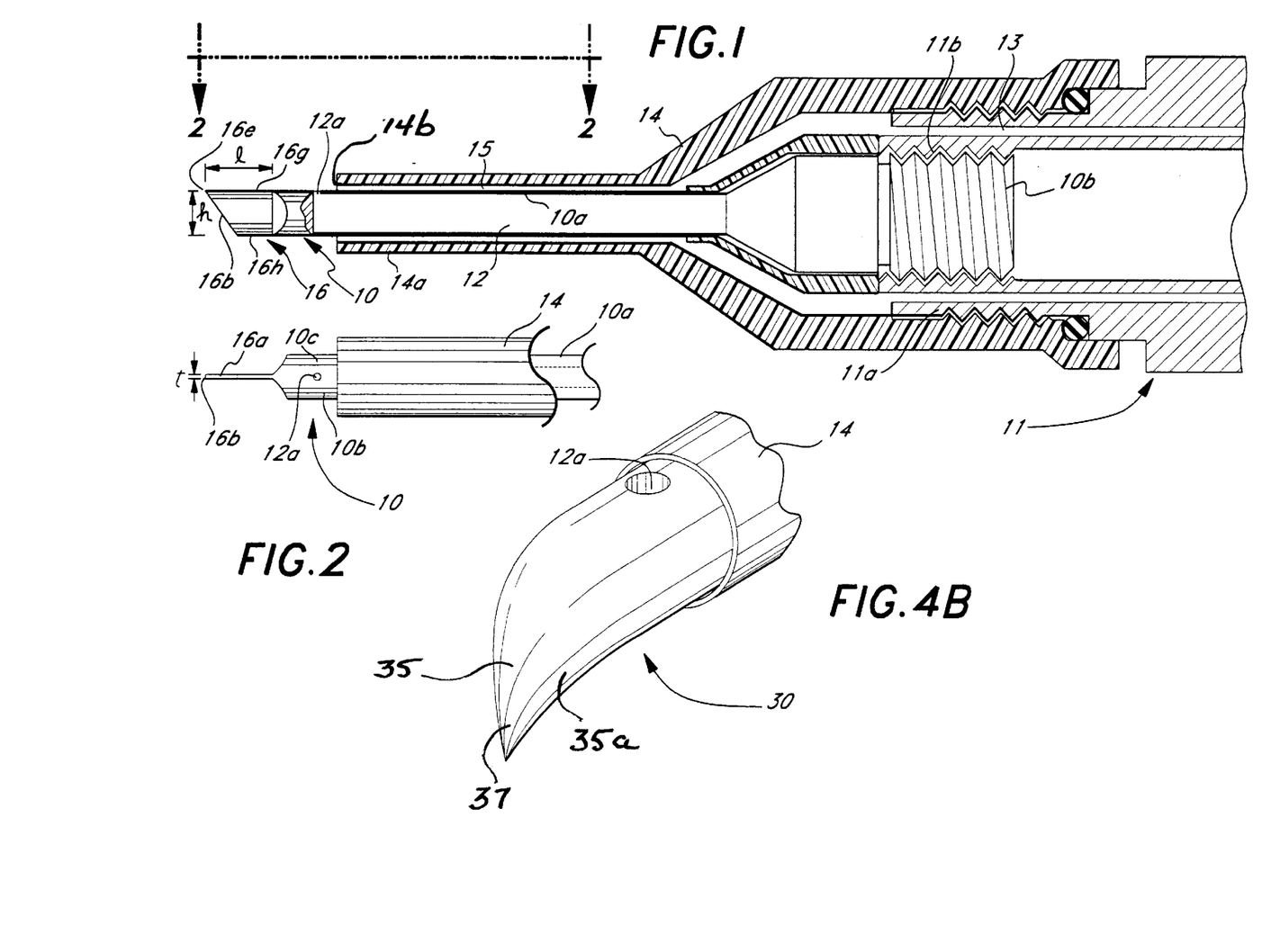
FIG. 1 is a side elevational view, partially in cross-section, of the first embodiment of the ophthalmological device of this invention.
FIG. 2 is a plan view of the first embodiment of the ophthalmological device of this invention taken along line 2—2 of FIG. 1.
FIG. 4B is a perspective view of the third embodiment of the ophthalmological device of this invention.

As depicted in FIG. 1, the phaco tip 10 of this invention is connected to a conventional phaco handpiece 11 which includes an ultrasonic horn 11a having an open threaded end 11b. The phaco tip 10 has a cylindrical body 10a with an open, threaded, proximal end 10b screwed into the end 11b of the horn 11a. A hallow passageway 12 extends from the proximal end 10b of the tip 10 to an aspiration port 12a in a side 10b (FIG. 2) of the body 10a. This aspiration port 12a allows material to be drawn into the passageway 12 when aspiration is selectively applied to the phaco tip 10. The aspiration port 12a has a diameter of about 0.4 mm. The cylindrical body 10a has a diameter of about 1.5 mm. The passageway 12 has a diameter of about 1.3 mm.

Figure 3:
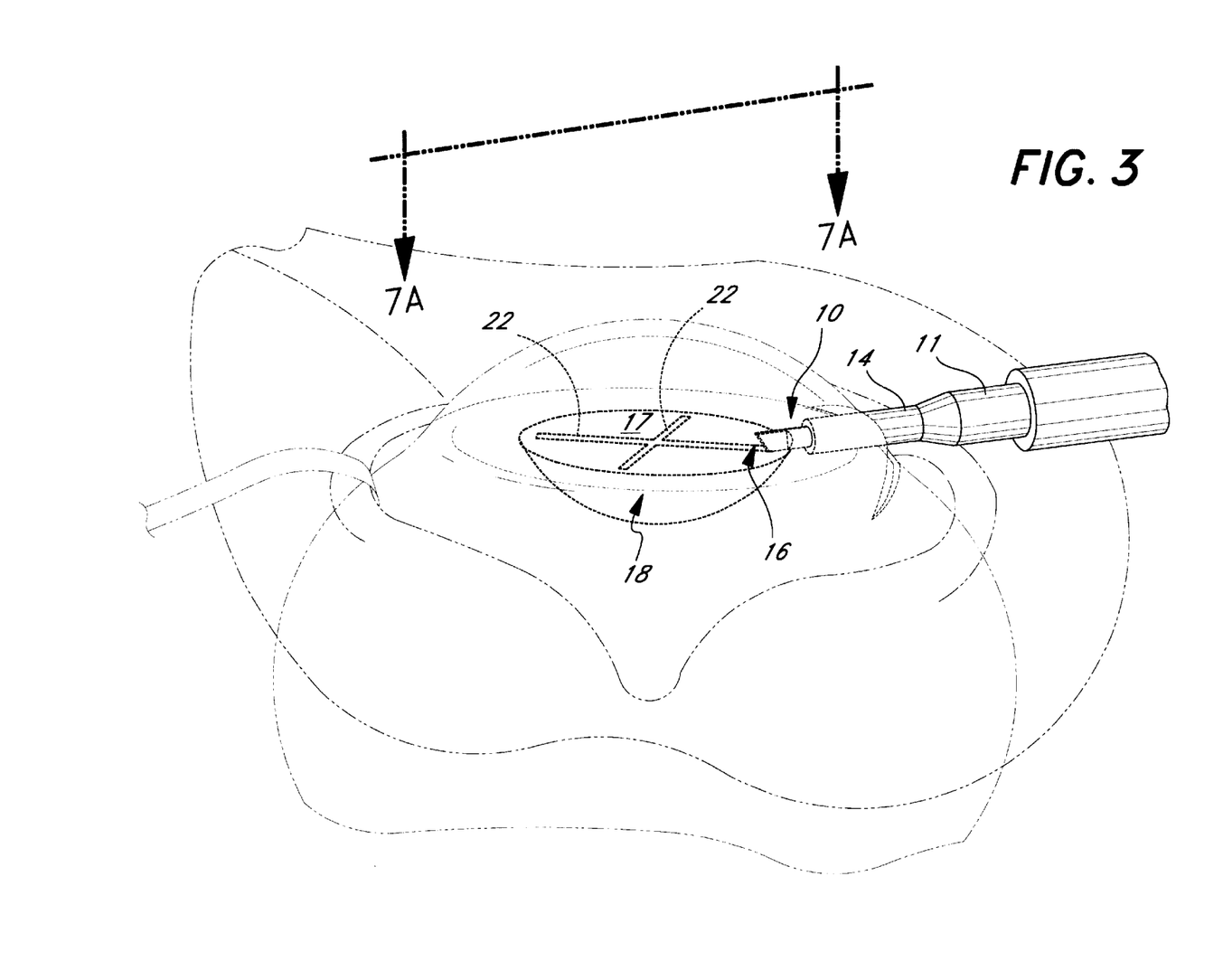
FIG. 3 is a schematic illustration of an eye showing a cataract nucleus cross cut in accordance with the method of this invention using the ophthalmological device shown in FIGS. 1 and 2.

A plastic sleeve 14 fits over the phaco tip 10, allowing the forward portion 10c of the phaco tip 10 to extend outward from this sleeve. The sleeve 14 has a cylindrical, tubular forward section 14a through which the phaco tip 10 extends. This tubular forward section 14a terminates at an open end 14b in advance of the aspiration port 12a to allow material to be sucked into the port when aspiration is selectively turned on by the surgeon. In accordance with this invention, aspiration is turned on after a cross shaped groove 22 is cut into a cataract nucleus 18 as illustrated in FIG. 3. The width of each groove 22 is about 0.4 mm and the depth of each groove is slightly over 50–60% of the thickness of the nucleus 18, typically about 3 mm. In the body of the horn 11a has an annular channel 13 through which water flows. As is conventional, the water is continuously supplied to the handpiece 11. This water flows through the channel 13 and passes between a gap 15 between the inside of the tubular forward section 14a and the body 10a of the phaco tip 10. The water serves to irrigate the eye as surgery is conducted.

At the distal end of the body 10a opposite the threaded end 10b is a solid, substantially flat, blade 16 which is aligned with the central longitudinal axis of the phaco tip 10. This blade 16, if not beveled, is sort of like a blunt knife. Preferably, however, it is beveled. The blade 16 has a thickness $t_1$ (FIG. 2) of about 0.4 mm, a height $h_1$ of about 1.5 mm, and a length $l_1$ of about 2.5 mm. The blade 16a can be made even thinner than 0.4 mm (and will thus use even less ultrasonic energy), but it is desirable to have some thickness to the groove 22 (FIG. 3) being cut so that the surgeon can see directly down into the base (not shown) of a freshly cut groove and check what he or she is cutting. However, theoretically preset depth cuts could be made with very thin blades 16 that can cut through the hardest nucleus with ease.

Preferably the aspiration port 12a is aligned with the top edge 16a of the blade 16. The aspiration port 12a is a distance from the apex 16e of the blade 16 of about 2.5 mm. The aspiration port 12a provides aspiration of any cavitation bubbles formed during the groove making step. The edges 16g and 16h are smooth and rounded. The front, beveled edge 16b of the blade 16a has a surface area of about 0.6 square millimeters. The front beveled edge 16b of the phaco tip 10 preferably has an angle of about 30° with respect to the longer, top edge 16a.

As shown in FIG. 3, the phaco tip 10 is normally used to cut the grooves 22 with the beveled edge 16b pointing downward away from the cornea and pressing against the face 17 of the cataract nucleus 18. This keeps the ultrasound energy transfer from the edge 16b of the blade 16 to the face 17 (FIG. 3) of the cataract nucleus 18 as efficient as possible. In accordance with this invention, there is usually no aspiration during the groove making step. The ultrasonic energy is directed into the nucleus 18 for better emulsification and at the same time the corneal endothelium is protected. Tubular, thin walled conventional phaco tips do not transfer energy well, and during phaco, one can see a "coring effect" where a cylindrical core like material is cut from the nucleus 18. This is because the only phacoemulsification occurring is at the rim of a conventional phaco tip. The new phaco tip 10 emulsifies the entire surface area at the beveled edge 16b of the blade 16, thus producing a true groove-type cut in the cataract nucleus 18. The phaco tip 10 with its flat blade 16 is able to chop (or cut) the nucleus, even a very hard nucleus, with very modest energy expenditure, for example, less than 30 sec. of ultrasound exposure. The energy requirement diminishes by the square of the thickness of the edge 16b of the blade 16.

The Debulking Tip

In accordance with one aspect of the method of this invention, the grooves 22 are first cut into the surface of the nucleus 18 and then a forceps such as, for example, an Akoshi pre-chopper or Katena nucleus cracker 19 is used to crack the nucleus into quarters. A suitable forceps may be purchased from Katena Instruments. Conventional phaco emulsification instruments are provided with two handpieces. One of these handpieces should be equipped with the phaco tip 10 and the other with a standard phaco tip. After segmenting the nucleus 18 and cracking it, the handpiece with the standard phaco tip is used to collected the segmented nucleus. Since there is no need to cut a groove with this standard tip, a zero degree bevel is most efficient with high vacuum to grasp each segmented piece of the nucleus after it has been cracked. As one can see, by separating the two steps, cutting and debulking, one can use tips designed much more efficiently for each step and thus allow safe use of this technique in very hard cataracts.

Second and Third Embodiments of Phaco Tip

Figures 4A, 5A, 5B:
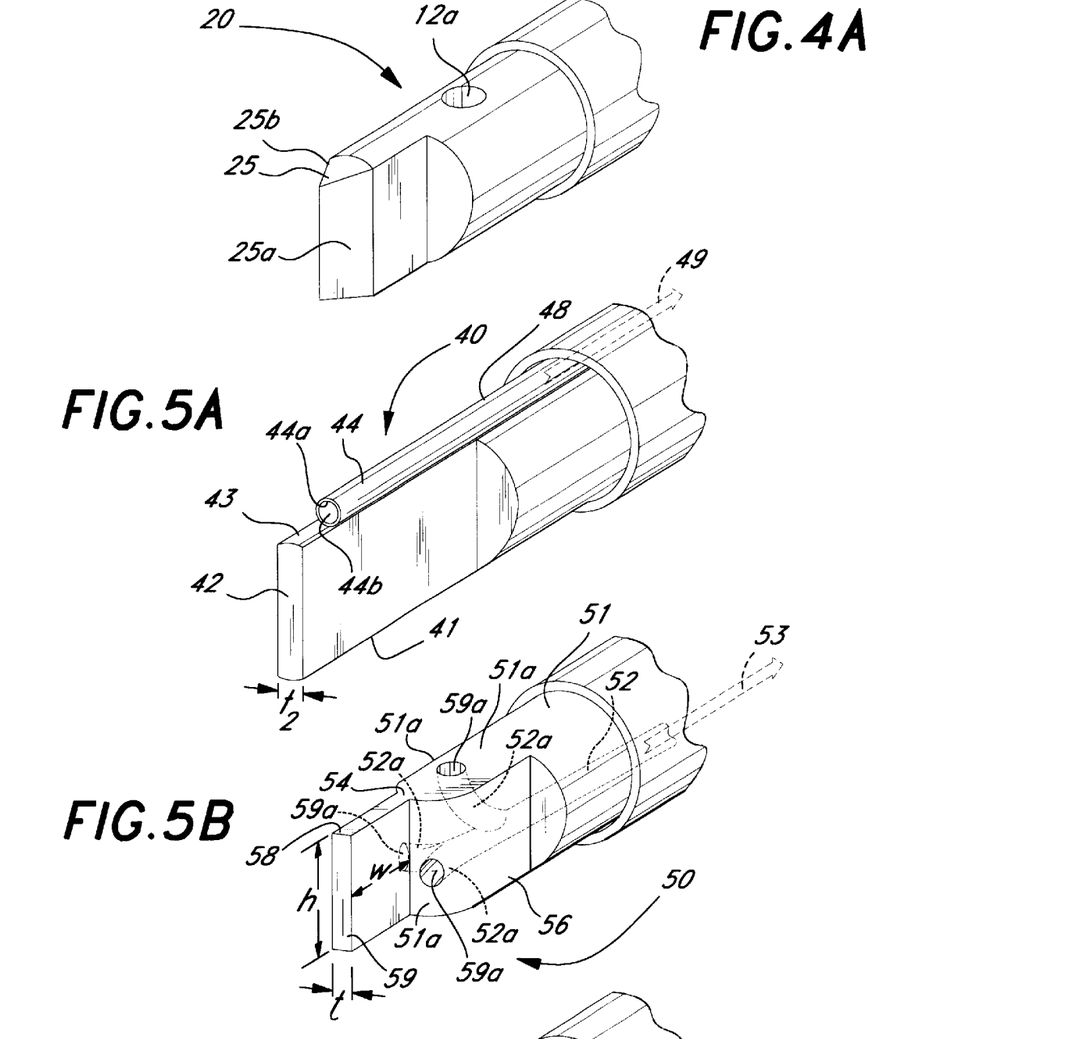
FIG. 4A is a perspective view of the second embodiment of the ophthalmological device of this invention.
FIG. 5A is a perspective view of the fourth embodiment of the ophthalmological device of this invention.
FIG. 5B is a perspective view of the fifth embodiment of the ophthalmological device of this invention.

As illustrated in FIG. 4A, the tip 20, which is substantially the same as tip 10, has a blade 25 which has a chisel shape.

The opposed sides 25a and 25b taper to an edge that extends along a line. This line is a right angle to the longitudinal axis of the tip 20.

As illustrated in FIG. 4B, the tip 30, which is substantially the same as tip 10, has a blade 35 is the shape of a claw. The side 35a, the face edge of the claw blade 35, is substantially conical, but bent like a claw. The blade 30 terminates at its apex 37 in a point. This design better enables the surgeon to cuts grooves by moving the tip 30 in and out relative to the nucleus 18 and from side to side.

Fourth and Fifth Embodiments of Phaco Tip

As illustrated in FIG. 5A, the tip 40 has a thin sold body 41 terminating in a flat, non-beveled face 42 having a rectangular configuration. Along one side 43 of the body 41 is a tubular member 44 providing a passageway 44a for aspiration which terminates in an opening 44b that is offset rearward from the face 42 by a distance of about 2 mm. A proximal end 48 of the passageway 44a is connected to a source of aspiration 49. The body 41 has a thickness $t_4$ of about 0.4 mm and a height of about 1 mm. The outside diameter of the tubular member 44 is about 1 mm.

As illustrated in FIG. 5B, the tip 50 has a body 51 with an internal, main passageway 52 (shown in dotted lines) connected to a source of aspiration 53. The body has sidewalls 51a and a rearward portion 56 connected by a neck 54 to a forward, block portion 58 that terminates in a flat face 59 having a rectangular configuration. The thickness t of the face 59 is about 0.4 mm and the height of the face is about 1 mm and the width w of the face is about 1.75 mm. In three of the sidewalls 51a are openings 59a (one shown in dotted lines) which connect through sub-passageways 52a to the main passageway 52. When the aspiration is turned on, debris is drawn into the sub-passageways 52a and then into the main passageway 52.

Method of This Invention

The method of this invention for removing a nucleus 18 of a cataract from an eye is shown in FIGS. 7A through 7E. A wound or opening 28 (3 mm or less in length) is made in the cornea to allow insertion through the opening 28 of the blade 16a and the sleeve 24. The nucleus 18 is then mobilized using conventional surgical techniques so that it may be rotated. using the phaco tip 10 attached to one handpiece 11 of a conventional phaco emulsification instrument, the blade 16 is inserted through the opening 28 and ultrasonic energy is provided to the blade while making a first incision or groove 22a across substantially the entire width of the nucleus 18 at a depth not to exceed about 3 millimeters while irrigating the nucleus with water flowing out the open end 14b of the sleeve 14, over the nucleus, and exiting through the opening 28.

One advantage of this blade 16 is the lack of aspiration since the blade is solid. The aspiration port 12a serves only to remove bubbles that may block the surgeon's view. At first though this may appear to be a disadvantage as one may wonder about removing debris from the eye as the cutting action proceeds. In reality, however, because of the blade 16 is so thin, very little nuclear material is actually being cut so visibility is not hampered at all. Secondly, there is continuous irrigation of fluid into the eye via the sleeve 14. The influent fluid is washed out of the eye through the entry wound or opening 28 between the sides of the sleeve 14 and the edge of the cornea 30 inside the entry wound 28. What little debris does form during the cutting action is easily washed out of the eye along with this flow of fluid. However, because there is virtually no aspiration, the blade 16 can be allowed to cut nuclei very close to the edge of the papillary iris with out fear of aspiration of the iris (not shown) into the aspiration port 12a as is always the danger with standard hollow passageway phaco tips. Thus one can cut the nucleus right adjacent to the iris with impunity. If the tip 10 touches the iris edge however by mistake, the papillary sphincter muscle gets cut and a slightly irregular pupil is noted.

Also, because of the absence of substantial aspiration, the blade 16a can be rotated so that it is positioned with its bevel edge 16c facing down thus allowing most of the ultrasonic energy to be directed down into the nucleus 18 rather than be directed up towards the cornea. Because of the virtual absence of aspiration, there is no fear of the posteria capsule or other vital structures being drawn towards the cutting blade 16 inadvertently. The cutting action is much more efficient with the bevel down position of the blade 16.

After making the first incision, the nucleus 18 is rotated substantially 90 degrees and then, while providing ultrasonic energy to the blade 16, a second incision 22b is made at substantially a right angle to the first incision 22a across the nucleus at a depth not to exceed about 3 millimeters while irrigating the nucleus with fluid flowing out the sleeve 14, over the nucleus, and exiting through the opening 28.

After making the cross incision, the nucleus 18 is cracked by inserting into the incisions 22a and 22b an instrument such as a forceps 19 which is manually manipulated to apply pressure against the internal walls 30 (FIG. 7E') of the incisions to break the nucleus into segments. It is often possible to rotate the device 16 around its longitudinal axis to split the nucleus along the incisions 22a and 22b thus made. In any case a regular nucleus splitter or forceps 19, for example, the Katena nucleus cracker, can then be inserted into the narrow grooves 22 to split the nucleus apart very easily if it refuses to split apart just with rotation of the blade 16. Because the grooves or incisions 22a and 22b being cut are now very narrow, there is one more minor advantage. During the cracking step the displacement of the cross action of the arms of the forceps 19 is a very small distance to crack and separate the nucleus completely, thus making the next step of debulking much easier.

Finally, a standard phaco emulsifier instrument with a standard phaco tip 21 is inserted through the opening 28 to emulsify the segments and withdraw the emulsified segments from the eye.

To make this procedure efficient, it is recommended that the two phaco handpieces provided with all standard phaco machines be utilized as discussed above. The first handpiece has attached to it the phaco tip 10 and the second handpiece has attached to it a standard aspiration phaco tip. After using the first handpiece with the phaco tip 10, simply pull it out of the eye, crack the nucleus 18, and then use the second handpiece to complete the phacoemulsification. During the cracking step, there is ample time for the surgical nurse to unplug the first handpiece from the phaco machine and plug in the second hand piece. It is not necessary to remove the phaco tip 10 from the first handpiece to attach the second tip to the second handpiece The height of the irrigating bottle and the leakiness of the corneal incision determines the depth of the anterior chamber since there is no aspiration involved. Generally a 3.5 keratome is used to enter the eye of the clear corneal limbus. The bottle height usually is set between 40 and 60 inches, adjusting it to keep the anterior chamber of the eye well maintained. Again, due to absence of aspiration, chamber height is easy to maintain by adjusting the bottle height.

Single Handed Surgical Technique

Preferably, a single handed technique is employed. No new skills need to be learnt and there is no learning curve as when learning to do manual phaco chop technique. The steps involved are as follows:

1. Use both handpieces supplied with the machine (normally one is kept as a spare.) Connect the phaco tip 10 to one handpiece and the standard aspiration phaco tip 14 to a second handpiece. Plug in the first hand piece into the machine, tune it if needed just like one normally does and have it ready for use by connecting the I-A (Irrigation and Aspiration) lines. Do regular cataract surgery until capsulorhexis and hydrodissection are done. Occasionally there will be a small amount of cortex on the anterior lens surface that will obscure the view during the cutting step. The solid blade 16 can be used lightly on the surface of the soft cortex to emulsify and wash it out easily if it obscures the view.

2. Use a little viscoelastic to push the iris down and slide the solid device 16 sideways into the eye.

3. Set the bottle height with irrigation on to a comfortable anterior chamber depth (generally between 40 and 60 inches).

4. Rotate the tip to bevel edge 16b into a down position with the aspiration port 12a pointing up.

5. When ultrasound is turned on, the phaco tip 10 will cut the nucleus 18 with great ease. Move back and forth in the groove to go deeper up to the iris edge but not to touch it. The iris sphincter will get cut if inadvertent contact is made with the tip.

6. Push down gently and move back and forth gently till the entire tip is buried for the length of the cut. Figure cutting a length approximately 4–5 mm long depending on the pupillary dilation and diameter of the capsulorhexis. The length is not critical as the nucleus cracker will split the nucleus easily.

7. Turn the nucleus 90 degrees and make the second cut. Pull out the phaco tip 10, put some viscoelastic and crack the nucleus 18 into quarters.

8. During this maneuver the surgical nurse unplugs this handpiece from the machine and plugs in the second handpiece that has the standard aspirating phaco tip 21.

9. Use the standard handpiece 21 with zero degree bevel tip and high vacuum. Aspiration of each quarter into the pupillary center is easy since the cracking step allows each piece to be separated completely.

Use in Poorly Dilated Pupils

The phaco tip 10 is ideal in cases where patients have been on miotics and pupil dilation is less than adequate. Since there are no aspiration concerns, it is possible to cut nucleus 18 even under and behind the pupillary edge without fear of breaking capsule. After the grooves are made, cracking and subsequent segmental debulking are much easier.

Design Considerations

The reasoning behind the design of this blade 16 is as follows. Firstly, by making the blade 16 very thin, a minimal amount of ultrasonic energy is used to cut through the hardest of nuclei 18 with ease (sort of like a chisel with a jack hammer effect). Ultrasound time to cut a 2.5 mm deep "cross" pattern takes less than 30 seconds. An exposed length of cutting blade 16 of 2.5 mm is extremely safe since average nuclei 18 are 4 to 4.5 mm deep. The blade 16a is used with the beveled edge 16b facing down as shown in FIG. 3. Since the blade 16 is solid with no aspiration at the apex, there is no risk of aspirating and damaging the iris, posterior capsule or other important structures. The bevel edge 16b is placed face down so that all of the ultrasonic energy is directed into the nucleus 18. Because the conventional phaco handpiece, which is used to hold the phaco tip 10, is usually at about 45 degrees to the iris plane (in a clear corneal approach), the blade 16 ends up approximately parallel to the nucleus surface and the entire 1.5 mm tip height $h_1$ is used to cut through the nucleus instead of just the apex 16e of the beveled edge 16b.

The 0.4 mm aspiration port 12a allows some recirculation of fluid to cool the blade 16a internally and at the same time it will remove any cavitation bubbles as described above. Another major advantage of a 0.4 mm cutting blade 16 thickness $t_1$ is that the amount of material being actually cut is very small and is released as a fine plume of "liquid smoke" which is instantly washed away as the cutting proceeds. Irrigation fluid from the sleeve 14 coming into the eye is washed out between the blade 16 and the corneal entry wound. The idea here is completely different from the "microseal" concept where aspiration and inflow rates are equal with no fluid being washed out of the corneal wound. In such a "microseal system" obstruction of the aspiration process can result in undue tip heating and resultant corneal burn. In accordance with this invention, since there is no significant aspiration, the corneal wound 28 (3.2 mm) is intentionally leaking so all of the fluid leaks out of the eye. The chamber depth is easily set by adjusting bottle height and remains steady throughout the cutting process since no significant aspiration goes on.

Figure 7A:
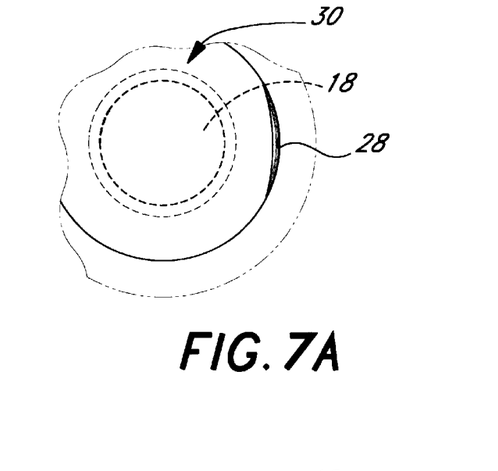
FIGS. 7A through 7F illustrate the method of this invention for removing a cataract nucleus from an eye.
Figures 7B, 7E:
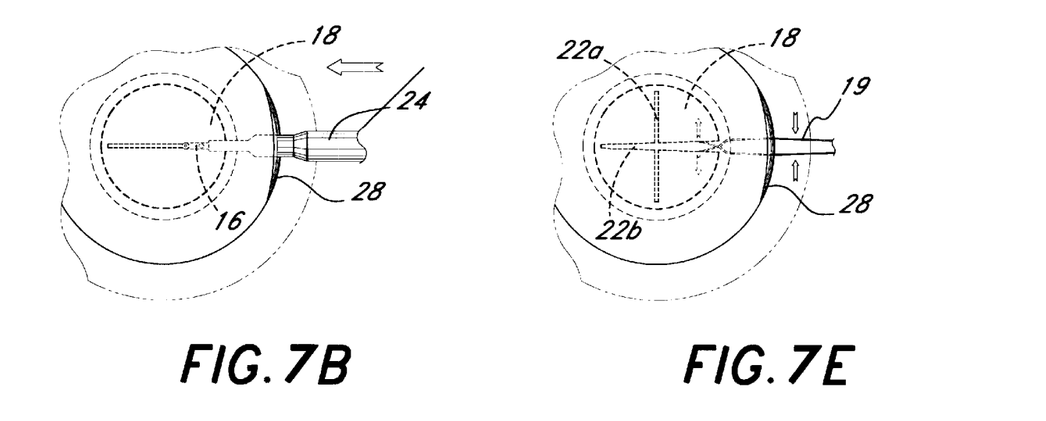
Figure 7C:
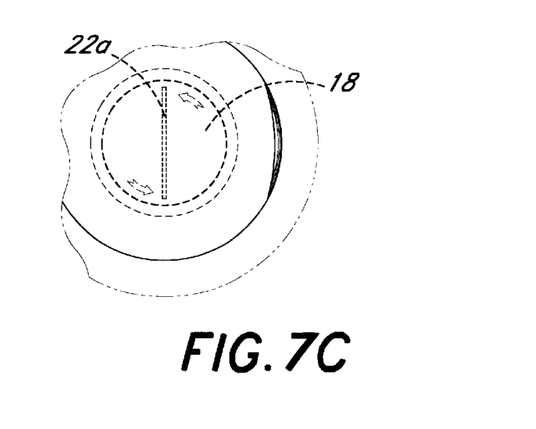
Figure 7D:
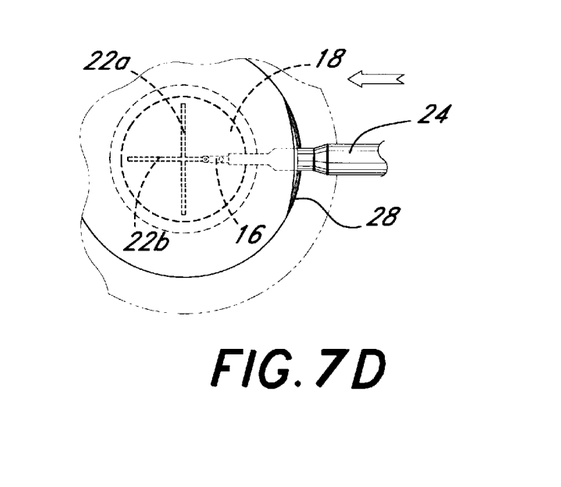
Figure 7E:
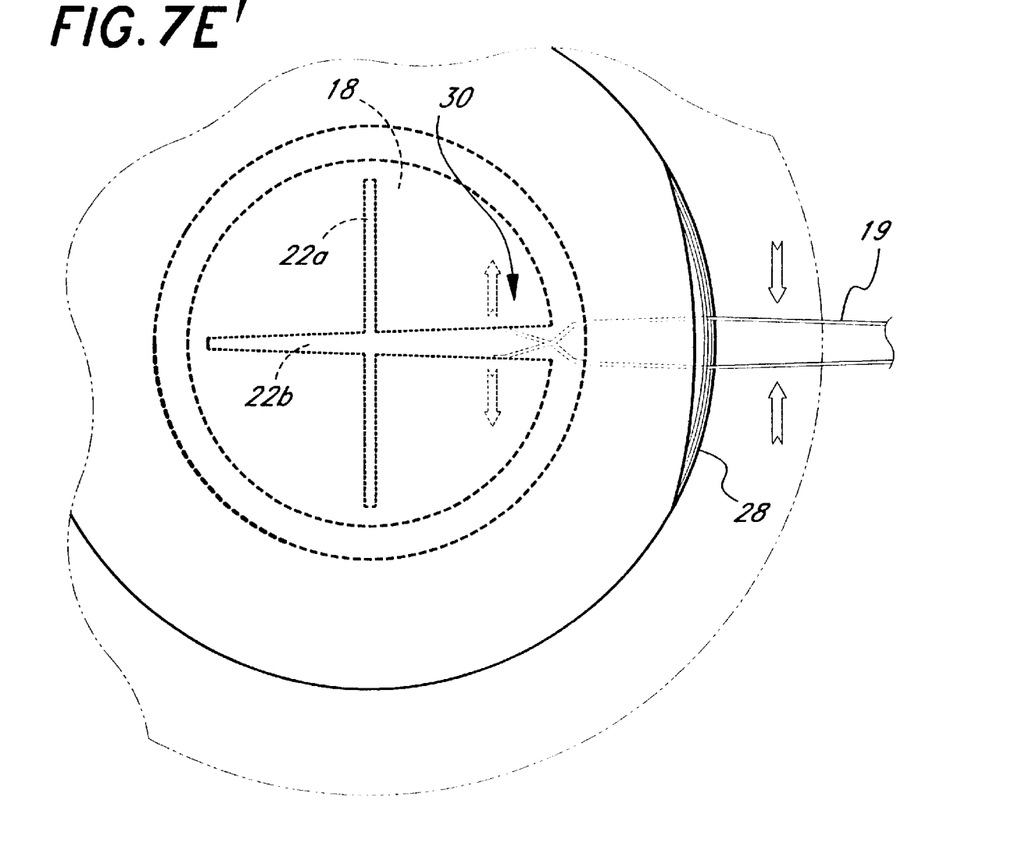
Figure 7F:
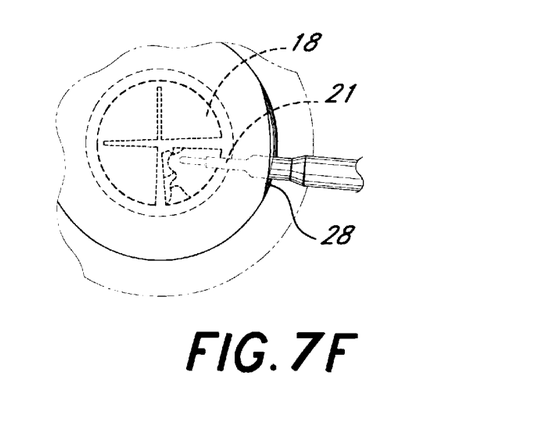

Because the groove 22 being cut is now very narrow, there is a minor advantage. As depicted in FIG. 7E, during the cracking step the displacement of the cross action forceps of the nucleus cracker need be only a very small distance to crack and separate the nucleus easily without unduly stretching the capsular bag.

Some of the important features of this phaco tip 20 are:

(1) A narrow (0.4 mm) thickness $t_1$ allows ease of cutting a hard nucleus 18. The resultant narrow groove 22 allowed easy and safe cracking.

(2) A solid blade 16 with no hollow passageway terminating in the face edge 16b enables the entire face edge to transfer ultrasonic energy and emulsify the nucleus area in contact therewith.

(3) Since there is no aspiration at the face edge 16b, there is:

(a) No risk of inadvertent aspiration and damage of iris, posterior capsule, anterior capsule edge, etc.

(b) The phaco tip 10 can be used with the beveled edge 16b down thus allowing all ultrasonic energy to be directed into the nucleus where it was needed and at the same time minimize exposure of the corneal endothelium to ultrasonic energy which is directed at the cornea in standard phaco tips that have aspiration and so require that they be used use in the bevel up position.

In hard nuclei, cutting an initial groove for a "groove and crack" approach has become very simple using the phaco tip 10. Also, without aspiration, the phaco tip 10 can be placed bevel down so that the face edge 16b of the tip is flush with the nucleus being cut. Since phaco energy transfers to the nucleus 18 by direct contact, the solid surface area of the face edge 16b of the tip 10 allows maximum energy transfer into the nucleus. With the phaco tip 10 being only about 0.4 mm wide and the entire face edge 16b being solid (not hollow) the cutting efficiency is substantially enhanced and one can cut a narrow groove in the hardest of nuclei with minimal stress to the zonular framework, minimal exposure to the corneal endothelium, and no risk of inadvertent aspiration of structures such as iris, capsule etc.

After testing such a phaco tip 10 on a number of cataracts with different phaco machines, it was convincingly shown that in clinical practice such a solid tip works extremely well. Phaco times for making a groove (approximately 4–5 mm long and 2 mm deep) were 10–30 seconds. Since there is no aspiration, anterior chamber height can be maintained very stable with an initial bottle height setting that it does not change throughout the procedure. The fluid flows out of the eye between the sleeve 14 and the corneal wound 28 so there is no risk of a corneal burn.

Phaco technology has now reached a sophistication level where even the hardest cataract can be removed with phacoemulsification. However, it is critical to use the safest and easiest technique so that in difficult cases, excellent, repeatable results can be achieved. In this context it is clearly apparent that a multitip approach can provide a greater margin of safety without the need to learn complicated or difficult skills. In this respect, the new, substantially non-aspirating ultrasonic phaco tip of this invention offers a number of advantages over the standard, larger diameter, aspirating tip. The device of this invention can be made very narrow thus requiring very short ultrasound exposure time even for very dense cataracts. Risks of damaging the posterior chamber, iris and endothelium can be minimized. The device can be used with bevel facing down further protecting the endothelium and at the same time directing the ultrasonic energy into the nucleus where it is most needed. The narrow groove allows easy cracking without endangering the capsular bag. Lastly, since the chamber depth is set by the irrigation height, once set, chamber depth fluctuations are virtually eliminated.

Sixth Embodiment of Phaco Tip

Figure 6:
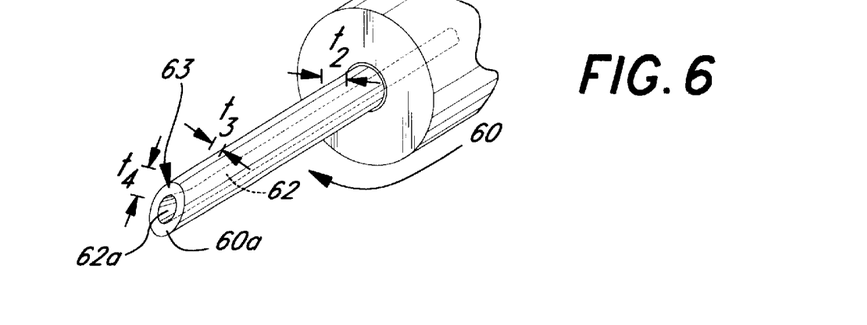
FIG. 6 is a perspective view of the sixth embodiment of the ophthalmological device of this invention.

As depicted in FIG. 6, the phaco tip 60 of this invention has a blade-like distal end with a thickness $t_2$ of about 0.4 mm. Thus, it retains the advantages of the narrow phaco tip 10. Additionally it includes an aspiration port 62a in the face edge 63. This aspiration port 62a is in communication with a passageway 62 that is connected to a source of aspiration, that is, a vacuum. The aspiration port 62a is a small, central oval opening 62a having, at its widest point, a width of about 1.6 mm and, at its narrowest point, a width of about 0.2 mm. The height of the face 63 is about 2.0 mm, leaving an equal wall thickness $t_4$ above and below the opening 62a. Thus, the width of the surfaces above and below the aspiration port 62a are each about 0.2 mm. The surfaces on each side of the opening 62a are of equal width, each being about 0.1 mm. This provides for an adequate metal to nucleus contact area, and keeps the ultrasound energy transfer from the phaco tip face 63 to face 17 (FIG. 3) of the nucleus 18 as efficient as possible. The face 63 of the phaco tip 10 preferably beveled at an angle of about 30°.

A disadvantage of the phaco tip 10 is that because of the lack of aspiration at the edge 16b it has no capacity to debulk or remove the segments of the nucleus that are created by cracking the nucleus. Thus, the standard phaco tip 21 with aspiration has to be used to finish the job of nucleus removal. The need to switch from the phaco tip 10 to a standard phaco tip during the course of the phaco procedure is inconvenient not withstanding the advantages of the solid, non aspirating phaco tip 10.

The new phaco tip 60 keeps all the advantages of the phaco tip 10. Specifically, the phaco tip 60 remains narrow having thickness $t_2$ at between 0.3–0.5 mm. However, because it has a hollow passageway 62, terminating in the beveled face 63 to permit aspiration. This allows the tip 60 to be used for the entire phacoemulsification procedure without the need to switch tips during the procedure. Aspiration, however, must be turned off while cutting the cross grooves 22. This is accomplished by modifications of the control unit 20 as discussed subsequently. The surgeon may turn aspiration on/off at will. This provides the advantages of not having aspiration continuously on, especially at the initial groove making stage and allows the tip 60 to be used bevel down (FIG. 3), thus protecting the endothelium from ultrasound exposure and directing ultrasonic energy directly into the nucleus 18, thereby enhancing the cutting process. At the same time there is no fear of inadvertent aspiration damage to the iris or capsule. Further, if at any time the view is compromised due to debris or air in the anterior chamber, the surgeon has complete control to turn aspiration on transiently to clean up the anterior chamber. During the debulking stage aspiration can be left on as with the standard tip 21 to allow flowability of nuclear pieces and their subsequent removal. This is achieved by depressing a special foot pedal 72 of the modified control unit.

The semi-solid, narrow phaco tip 60 has a key advantage in that its entire face 60a is placed in contact with the nucleus 18. Consequently, this tip 60 gives maximum cutting efficiency.

Control Unit

Figure 8:
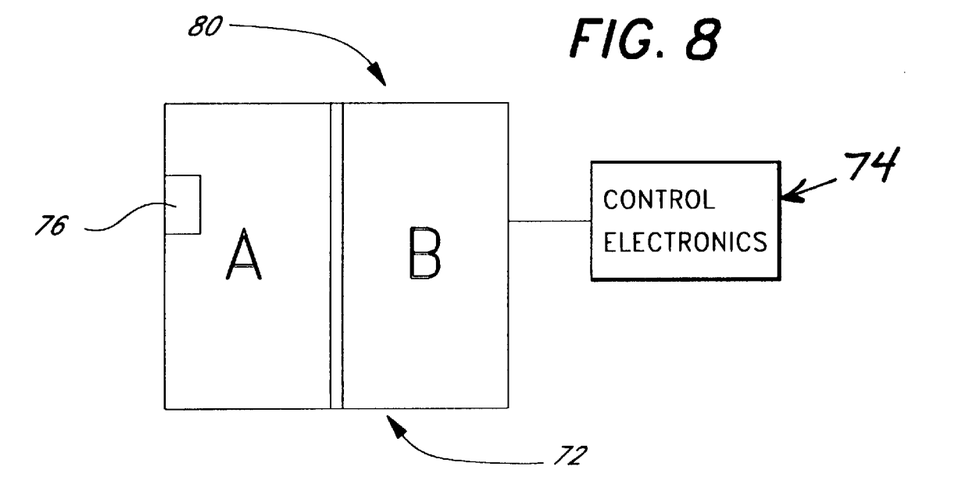
FIG. 8 is a schematic plan view of a conventional control unit modified in accordance with this invention to provide selectable aspiration.

As illustrated in FIG. 8, the control unit 80 incorporates a special foot pedal 72 and appropriate control electronics 74. The foot pedal 72 has a special section that allows the surgeon to switch on and off aspiration for a few seconds during the initial groove cutting step by actuation of a side switch 76. This remains completely under the surgeon's control to allow turning aspiration on and off any time he or she chooses. The foot pedal 72 contains two halves (Sections A and B). The surgeon's foot is placed on Section A initially and used during the groove cutting step to provide phaco energy to the tip. In this section A, the pedal 72 has only two positions only. Pressing down through Position 1 gives irrigation only, pushing down further to Position 2 adds increasing linear phaco power as the pedal is pressed down harder. The side switch 76, when actuated, turns on aspiration as needed to allow clearing of air bubbles or debris which enter the opening 62a and flow through the passageway 62. Section B of the pedal is the conventional 1, 2, 3 position pedal. Position 1 gives irrigation only, position 2 adds aspiration, and position 3 ads linear phaco power as in all conventional machines to allow debulking of the nuclear segments.

The control unit 80 of a conventional phaco machine, unlike all current machines, is designed to allow phaco without aspiration. In contrast, all currently used machines require aspiration to be present when phaco power is turned on. The advantage of having this new arrangement is that all the advantages of a thin, non aspirating phaco tip are still preserved, and yet, on occasion, when aspiration is desired, it is instantly available. It is also possible to do the entire phaco procedure with this tip 60, whereas the phaco tip 10 can only be used to cut an initial groove in the nucleus 18. The phaco tip is the only part of the phaco machine that does anything for the patient. Up to now, the need for aspiration has been taken for granted, thus necessitating tips with all the built in disadvantages discussed earlier. Once the aspiration step is dissociated from the phaco step, the narrow phaco tip 10, beveled face 63 facing down may be used. This increases the surface contact area and greatly increase the cutting efficiency during the groove making step when working with a very hard cataract nucleus.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention.

What is claimed is:

1. A method of removing a nucleus of a cataract from beneath the cornea of an eye, comprising
   (a) making an opening in the eye to provide access to the nucleus and allow insertion through the opening of a distal end of a first phaco tip having a solid blade with a face edge adapted to be placed in contact with the nucleus, said face edge characterized in that it does not have any aspiration port therein,
   (b) inserting the blade of the first phaco tip through the opening and providing ultrasonic energy to the blade while making at least one incision with the blade in the nucleus, said incision having internal walls,
   (c) cracking the nucleus by inserting into the incisions an instrument which is manually manipulated to apply pressure against the internal walls of the incision to break the nucleus into segments, and
   (d) inserting through the opening a second phaco tip including an aspiration port therein and applying aspiration while emulsifying the segments and withdrawing the emulsified segments through the aspiration port.

2. The method of claim 1 including irrigating the nucleus with water which exits through the opening.

3. An ophthalmological surgical instrument for cutting a nucleus of a cataract, including
   a handpiece having an ultrasonic horn that provides ultrasonic energy for cutting the nucleus, and
   a phaco tip connected to the ultrasonic horn so that the ultrasonic energy is transmitted via said tip to the nucleus,
   said tip including a body having at a distal end thereof a solid blade having a face edge adapted to be placed in contact with the nucleus and characterized in that the face edge does not have any aspiration port therein,
   said solid blade having a thickness no greater than 0.6 millimeters, so that said blade upon energization by the ultrasonic horn acts, upon contact with the nucleus, like a chisel.

4. The ophthalmological surgical instrument of claim 3 where the body has an aspiration port therein displaced rearward from said face edge by a distance greater than the length of the blade, said aspiration port positioned on the body to point away from the nucleus when the face edge is placed in contact with the nucleus.

5. The ophthalmological surgical instrument of claim 4 including a sleeve which fits over the body of the tip and has a forward section that terminates in an opening in advance of the aspiration port, so that the sleeve does not cover the aspiration port.

6. The ophthalmological surgical instrument of claim 3 where the blade has a claw shape.

7. The ophthalmological surgical instrument of claim 3 where the face edge has width and height dimensions which at their greatest dimensions do not exceed the width and height dimensions of the body of the phaco tip.

8. The ophthalmological surgical instrument of claim 3 where the face edge has a surface area from 0.4 to 0.8 square millimeters.

9. An ophthalmological surgical instrument for removing a nucleus of a cataract from beneath the cornea of an eye, comprising
   a source of aspiration,
   a handpiece having
      an ultrasonic horn that provides ultrasonic energy for cutting the nucleus, and
      a phaco tip connected to the ultrasonic horn so that the ultrasonic energy is transmitted via said tip to the nucleus,
      said tip including a body having at a distal end thereof a solid blade having a face edge adapted to be placed in contact with the nucleus and characterized in that the face edge does not have any aspiration port therein and has a surface area from 0.4 to 0.8 square millimeters,
      said solid blade having a length from 2.0 to 5.0 millimeters, a height from 1.0 to 3.0 millimeters, and a thickness from 0.1 to 0.6 millimeters, so that said blade upon energization by the ultrasonic horn acts, upon contact with the nucleus, like a chisel,
      said the body having an aspiration port therein displaced rearward from said face edge by a distance greater than the length of the blade, said aspiration port positioned on the body to point away from the nucleus when the face edge is placed in contact with the nucleus,
      said aspiration port being adapted to be placed in communication with the source of aspiration, and
   a control unit for regulating the application of aspiration to the aspiration port, enabling aspiration at the aspiration port to be turned on and off on command.

* * * * *